(12) United States Patent
Ochiai et al.

(10) Patent No.: US 8,119,983 B2
(45) Date of Patent: Feb. 21, 2012

(54) GC-MS ANALYZER SWITCHABLE BETWEEN ONE-DIMENSIONAL AND TWO-DIMENSIONAL MODES

(75) Inventors: Nobuo Ochiai, Tokyo (JP); Kikuo Sasamoto, Tokyo (JP); Hirooki Kanda, Tokyo (JP)

(73) Assignee: Gerstel K.K., Tokyo (JP)

( * ) Notice: Subject to any disclaimer, the term of this patent is extended or adjusted under 35 U.S.C. 154(b) by 434 days.

(21) Appl. No.: 12/424,831

(22) Filed: Apr. 16, 2009

(65) Prior Publication Data

US 2009/0261245 A1 Oct. 22, 2009

(30) Foreign Application Priority Data

Apr. 17, 2008 (JP) .................................. 2008-107892

(51) Int. Cl.
*H01J 49/00* (2006.01)
(52) U.S. Cl. ......................... 250/288; 250/281; 250/282
(58) Field of Classification Search .................. 250/281, 250/282, 288
See application file for complete search history.

(56) References Cited

U.S. PATENT DOCUMENTS

| | | | | | |
|---|---|---|---|---|---|
| 7,608,818 | B2 * | 10/2009 | Miller et al. | .................. | 250/288 |
| 2007/0031974 | A1 | 2/2007 | Jain et al. | | |
| 2007/0039375 | A1 | 2/2007 | Chaintreau et al. | | |

FOREIGN PATENT DOCUMENTS

| | | |
|---|---|---|
| EP | 0597602 A | 5/1994 |
| JP | H06-201670 | 7/1994 |
| JP | 2005-221341 | 8/2005 |
| JP | 2005-274416 | 10/2005 |
| JP | 2005-283403 | 10/2005 |
| JP | 2006064646 | 3/2006 |
| JP | 2006-226678 | 8/2006 |

(Continued)

OTHER PUBLICATIONS

Diehl, J.W. et al., "Determination of aromatic hydrocarbons in gasolines by flow modulated comprehensive two-dimensional gas chromatography," Science Direct, Elsevier (Paulsboro, NJ), p. 157-165, (Aug. 20, 2004).

(Continued)

*Primary Examiner* — Michael Maskell
(74) *Attorney, Agent, or Firm* — Hammer & Associates, P.C.

(57) ABSTRACT

One-dimensional GC-MS/olfactory analysis and two-dimensional GC-MS/olfactory analysis can be freely performed in one analyzer by a simple switching operation, without changing the device configuration. An odor component analyzer is used which includes a sample injection port equipped with a pressure control device, a GC first dimensional column connected to the sample injection port, a three-way connector $T_{1-2}$ connected to the GC first dimensional column, three-way connectors $T_{1-1}$, $T_{1-3}$ each connected to the three-way connector $T_{1-2}$, a solenoid valve connected to the three-way connectors $T_{1-1}$, $T_{1-3}$ and serving to adjust flow channels of the three-way connectors $T_{1-1}$, $T_{1-3}$, a first pressure control device connected to the solenoid valve, a three-way connector $T_{2-1}$ connected to the three-way connector $T_{1-3}$, a second pressure control device connected to the three-way connector $T_{2-1}$, a three-way connector $T_{2-2}$ connected to the three-way connector $T_{2-1}$, a three-way connector $T_{2-3}$ connected to the three-way connector $T_{2-2}$, a mass analyzer and an olfactory device each connected to the three-way connector $T_{2-3}$, and a GC second dimensional column connected to the three-way connector $T_{1-1}$ and the three-way connector $T_{2-2}$.

7 Claims, 12 Drawing Sheets

FOREIGN PATENT DOCUMENTS

JP 2006-226679 8/2006
WO WO 2005/111599 A1 11/2005

OTHER PUBLICATIONS

Tohru Matsumura, Russel Kinghorn, "Determination of Dioxins and Related Compounds using Multi Dimension GC-HRMS", 8th Symposium on Environmental Chemistry Program and Abstracts, Jul. 7, 1999, p. 104-105.

"ODP2—Olfactory Detector Port," Catalogue for Introduction System for Thermal Desorption, Gerstel Co., (pp. 16-17).

"Gerstel Separation," Excellent Solution Catalogue, Gerstel Co., (pp. 14-15).

"Master the GC—Q & A Separation and Detection", "Gasu Kuro Jiyu Jizai", Maruzen Co., (p. 89).

* cited by examiner

GC-MS ANALYZER SWITCHABLE BETWEEN ONE-DIMENSIONAL AND TWO-DIMENSIONAL MODES

BACKGROUND OF THE INVENTION

1. Field of the Invention

The present invention relates to a gas chromatography-mass spectrometry analyzer (GC-MS). More particularly, the present invention relates to a GC-MS device that can identify a target component by easily switching a gas chromatograph (GC) between a one-dimensional mode and a two-dimensional mode, without changing the device configuration. The present invention also relates to a device that can identify an odor component by easily switching a gas chromatograph (GC) between a one-dimensional mode and a two-dimensional mode, by using GC-MS and an olfactory device without changing the device configuration. Further, the device can be used as a device for identifying chemical substances of general use by replacing the olfactory device with another GC detector using the same device configuration.

2. Description of the Related Art

In recent years, issues relating to safety and health effects of food have been drawing increased attention, and one-dimensional GC-MS/olfactory devices have been introduced in a variety of fields relating to food, beverages, perfumes, packaging containers, automobiles, and automobile parts. In such analysis of odor components, identification is carried out by using GC or GC-MS and performing analysis in combination with an olfactory device (Catalogue for Introduction System for Thermal Desorption, GERSTEL Co., pages 16, 17) that is attached to the GC outlet portion (one-dimensional GC-MS/olfactory analysis; see FIG. 1, FIG. 2).

However, the requirements for such analysis are getting more stringent and analytical methods suitable for smaller amounts of odor components are needed. Accordingly, the separation attained with the one-dimensional GC-MS/olfactory device alone is insufficient and the demand for two-dimensional GC-MS/olfactory devices suitable for separating these components has been growing. In two-dimensional analysis, two-dimensional GC in which the second GC is connected (Excellent Solution Catalogue, GERSTEL Co., pages 14, 15; Maruzen Co. "Gasu Kuro Jiyu Jizai (Reference to Gas Chromatography)", page 89) is used when the separation with one GC is insufficient, and the identification analysis is performed by attaching a mass spectrometer (MS) and then an olfactory device to the outlet of the second GC in a similar manner (two-dimensional GC-MS/olfactory analysis; see FIG. 3, FIG. 4).

However, these one-dimensional GC-MS/olfactory analyzer and two-dimensional GC-MS/olfactory device are separate devices, and two expensive systems have to be available to perform analysis and identification of components with insufficient separation.

Analysis using a separate two-dimensional GC system also has to be conducted in the case when separation with one GC is insufficient in a general analysis other than odor analysis.

It is an object of the present invention to perform one-dimensional GC analysis and two-dimensional GC analysis in GC-MS by a simple switching operation, without changing the device configuration. Another object is to perform freely the one-dimensional GC-MS/olfactory analysis and two-dimensional GC-MS/olfactory analysis in a two-dimensional GC-MS/olfactory device by a simple switching operation, without changing the device configuration. Yet another object is to enable the switching between the one-dimensional GC analysis and two-dimensional GC analysis even in applications other than odor analysis.

The inventors have found that one-dimensional GC-MS/olfactory analysis and two-dimensional GC-MS/olfactory analysis can be freely performed by a simple switching operation, without changing the device configuration, by incorporating a mechanism performing a specific flow channel control in a two-dimensional GC-MS/olfactory device. Further, the inventors have found that one-dimensional GC-MS analysis and two-dimensional GC-MS analysis can be performed without changing the device configuration, by incorporating a mechanism performing a specific flow channel control in the same manner.

SUMMARY OF THE INVENTION

The present invention relates to an odor component analyzer, comprising: (a) a sample injection port equipped with a pressure control device; (b) a GC first dimensional column connected to the sample injection port; (c) a three-way connector $T_{1-2}$ connected to the GC first dimensional column; (d) three-way connectors $T_{1-1}$, $T_{1-3}$, each connected to the three-way connector $T_{1-2}$; (e) a solenoid valve connected to the three-way connectors $T_{1-1}$, $T_{1-3}$ and serving to adjust flow channels of the three-way connectors $T_{1-1}$, $T_{1-3}$; (f) a first pressure control device connected to the solenoid valve; (g) a three-way connector $T_{2-1}$ connected to the three-way connector $T_{1-3}$; (h) a second pressure control device connected to the three-way connector $T_{2-1}$; (i) a three-way connector $T_{2-2}$ connected to the three-way connector $T_{2-1}$; (j) a three-way connector $T_{2-3}$ connected to the three-way connector $T_{2-2}$; (k) a mass analyzer and an olfactory device, each connected to the three-way connector $T_{2-3}$; and (l) a GC second dimensional column connected to the three-way connector $T_{1-1}$ and the three-way connector $T_{2-2}$.

The present invention also relates to an odor component analyzer, comprising: (a) a sample injection port equipped with a pressure control device; (b) a GC first dimensional column connected to the sample injection port; (c) a three-way connector $T_{1-2}$ connected to the GC first dimensional column; (d) three-way connectors $T_{1-1}$, $T_{1-3}$, each connected to the three-way connector $T_{1-2}$; (e) a solenoid valve connected to the three-way connectors $T_{1-1}$, $T_{1-3}$ and serving to adjust flow channels of the three-way connectors $T_{1-1}$, $T_{1-3}$; (f) a pressure control device FPR1 connected to the solenoid valve; (g) a five-way connector connected to the three-way connector $T_{1-3}$; (h) a pressure control device FPR2, a GC second dimensional column, a mass analyzer, and an olfactory device, each connected to the five-way connector.

The present invention also relates to the above-described odor component analyzer, further comprising a device for adjusting a temperature of only a first dimensional column section and/or only a second dimensional column section.

The present invention also relates to an analyzer, comprising: (a) a sample injection port equipped with a pressure control device; (b) a GC first dimensional column connected to the sample injection port; (c) a three-way connector $T_{1-2}$ connected to the GC first dimensional column; (d) three-way connectors $T_{1-1}$, $T_{1-3}$, each connected to the three-way connector $T_{1-2}$; (e) a solenoid valve connected to the three-way connectors $T_{1-1}$, $T_{1-3}$ and serving to adjust flow channels of the three-way connectors $T_{1-1}$, $T_{1-3}$; (f) a first pressure control device connected to the solenoid valve; (g) a three-way connector $T_{2-1}$ connected to the three-way connector $T_{1-3}$; (h) a second pressure control device connected to the three-way connector $T_{2-1}$; (i) a three-way connector $T_{2-2}$ connected to the three-way connector $T_{2-1}$; (j) a three-way connector $T_{2-3}$ connected to the three-way connector $T_{2-2}$; (k) a mass analyzer and a GC detector, each connected to the three-way connector $T_{2-3}$; and (l) a GC second dimensional column connected to the three-way connector $T_{1-1}$ and the three-way connector $T_{2-2}$.

The present invention also relates to an analyzer, comprising: (a) a sample injection port equipped with a pressure control device; (b) a GC first dimensional column connected to the sample injection port; (c) a three-way connector $T_{1-2}$ connected to the GC first dimensional column; (d) three-way connectors $T_{1-1}$, $T_{1-3}$, each connected to the three-way connector $T_{1-2}$; (e) a solenoid valve connected to the three-way connectors $T_{1-1}$, $T_{1-3}$ and serving to adjust flow channels of the three-way connectors $T_{1-1}$, $T_{1-3}$; (f) a first pressure control device connected to the solenoid valve; (g) a five-way connector connected to the three-way connector $T_{1-3}$; (h) a second pressure control device, a GC second dimensional column, a mass analyzer, and a GC detector, each connected to the five-way connector.

The present invention also relates to the above-described analyzer, further comprising a device for adjusting a temperature of only a first dimensional column section and/or only a second dimensional column section.

The present invention also relates to the above-described analyzer, wherein the GC detector is selected from a group consisting of a FID, a NPD, an ECD, a SCD, a NCD, an AED, a FPD, and a PFPD.

The present invention also relates to an analyzer comprising: (a) a sample injection port equipped with a pressure control device; (b) a GC first dimensional column connected to the sample injection port; (c) a three-way connector $T_{1-2}$ connected to the GC first dimensional column; (d) three-way connectors $T_{1-1}$, $T_{1-3}$, each connected to the three-way connector $T_{1-2}$; (e) a solenoid valve connected to the three-way connectors $T_{1-1}$, $T_{1-3}$ and serving to adjust flow channels of the three-way connectors $T_{1-1}$, $T_{1-3}$; (f) a first pressure control device connected to the solenoid valve; (g) a three-way connector $T_{2-1}$ connected to the three-way connector $T_{1-3}$; (h) a second pressure control device connected to the three-way connector $T_{2-1}$; (i) a three-way connector $T_{2-2}$ connected to the three-way connector $T_{2-1}$; (j) a mass analyzer connected to the three-way connector $T_{2-2}$; and (k) a GC second dimensional column connected to the three-way connector $T_{1-1}$ and the three-way connector $T_{2-2}$.

The present invention also relates to the above-described odor component analysis, further comprising a device for adjusting a temperature of only a first dimensional column section and/or only a second dimensional column section.

In accordance with the present invention, one-dimensional GC-MS/olfactory analysis and two-dimensional GC-MS/olfactory analysis can be freely performed in a two-dimensional GC-MS/olfactory device by a simple switching operation, without changing the device configuration. Furthermore, in accordance with the present invention, analysis other than odor analysis can be also performed by switching between one-dimensional GC analysis and two-dimensional GC analysis.

DESCRIPTION OF THE PREFERRED EMBODIMENTS

Figure 5:
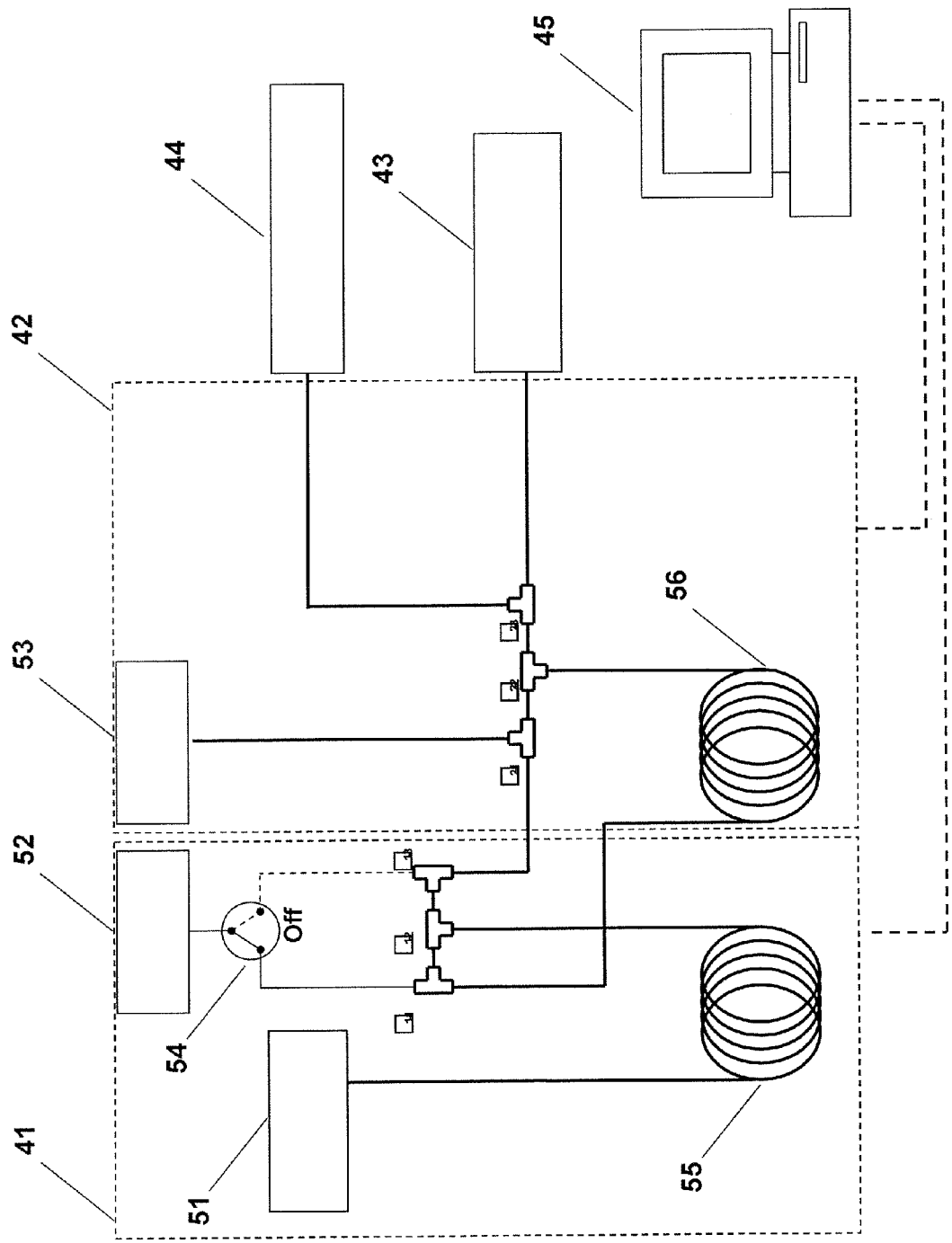
FIG. 5 illustrates the configuration in accordance with the present invention.

The present invention will be described below with reference to the appended drawings. FIG. 5 shows a schematic configuration of an odor component analyzer in accordance with the present invention. Referring to FIG. 5, the odor component analyzer in accordance with the present invention includes: (a) a sample injection port 51 equipped with a pressure control device; (b) a GC first dimensional column 55 connected to the sample injection port 51 equipped with a pressure control device; (c) a three-way connector $T_{1-2}$ connected to the GC first dimensional column 55; (d) three-way connectors $T_{1-1}$, $T_{1-3}$, each connected to the three-way connector $T_{1-2}$; (e) a solenoid valve 54 connected to the three-way connectors $T_{1-1}$, $T_{1-3}$; (f) a pressure control device 52 connected to the solenoid valve 54; (g) a three-way connector $T_{2-1}$ connected to the three-way connector $T_{1-3}$; (h) a pressure control device 53 connected to the three-way connector $T_{2-1}$; (i) a three-way connector $T_{2-2}$ connected to the three-way connector $T_{2-1}$; (j) a three-way connector $T_{2-3}$ connected to the three-way connector $T_{2-2}$; (k) a mass analyzer 43 and an olfactory device 44, each connected to the three-way connector $T_{2-3}$; and (l) a GC second dimensional column 56 connected to the three-way connector $T_{1-1}$ and the three-way connector $T_{2-2}$. The sample injection port 51, pressure control device 52, solenoid valve 54, three-way connectors $T_{1-1}$, $T_{1-2}$, $T_{1-3}$, and CG first dimensional column 55 constitute a first dimensional gas chromatograph 41. The pressure control device 53, three-way connectors $T_{2-1}$, $T_{2-2}$, $T_{2-3}$, and GC second dimensional column 56 constitute a second dimensional gas chromatograph 42. The odor component analyzer in accordance with the present invention is configured by a control computer 45 connected to the gas chromatographs 41 and 42.

Figure 6:
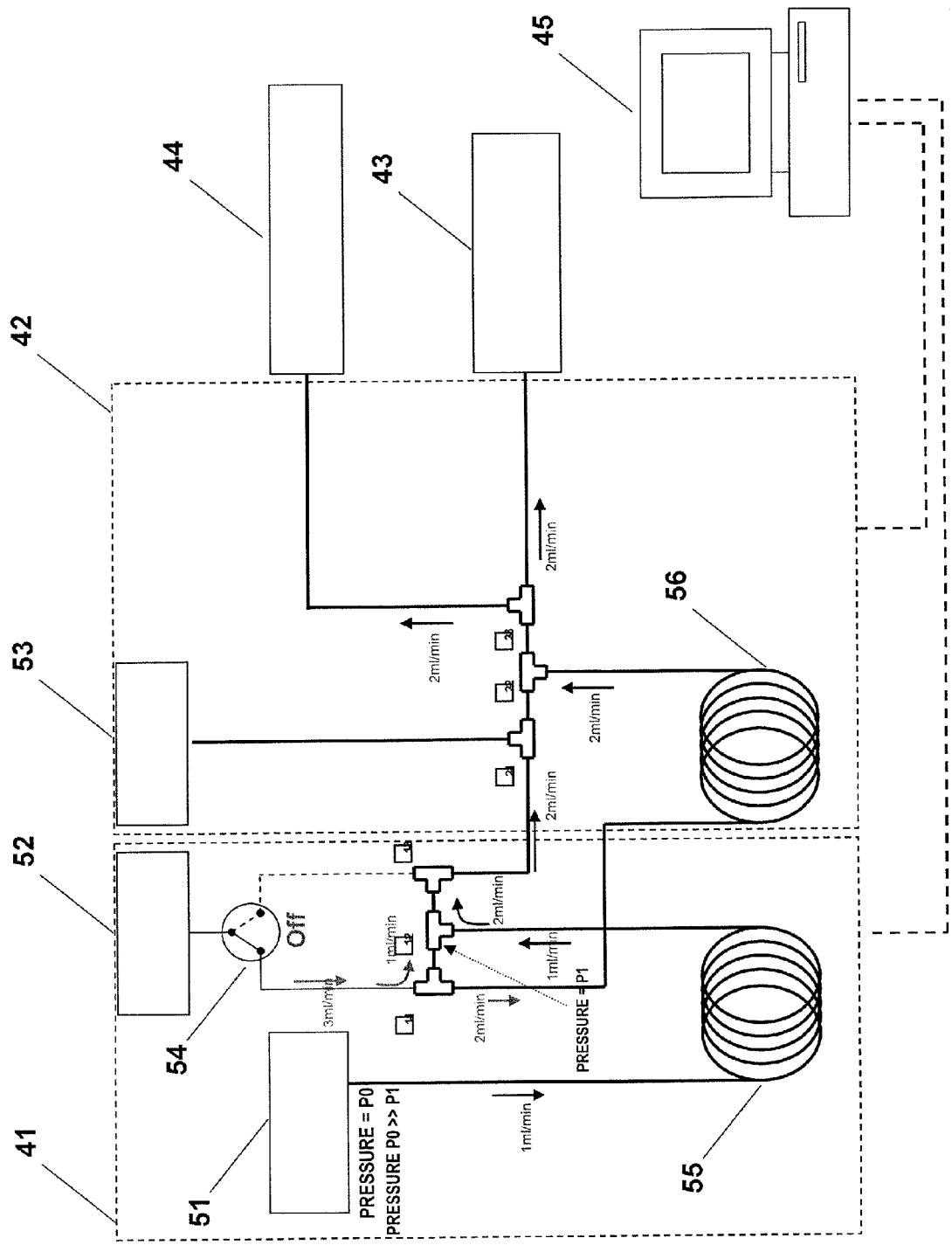
FIG. 6 illustrates the operation in accordance with the present invention.

The operation of the odor component analyzer in accordance with the present invention will be described below. First, an analysis method based only on a GC first dimensional column will be described. Referring to FIG. 6, a sample that is the analysis object is injected from a sample injection port 51 equipped with a pressure control device. A pressure P0 in the sample injection port in this case is set higher than a pressure P1 in the three-way connector $T_{1-2}$. The sample injected from the sample injection port 51 equipped with a pressure control device is introduced in the GC first dimensional column 55, separated correspondingly to the retention time, passes through the three-way connector $T_{1-2}$ and is introduced in the second dimensional gas chromatograph 42 via the three-way connector $T_{1-3}$. The switch of the solenoid valve 54 is in the OFF state, a moving phase gas flowing in from the pressure control device 52 passes through the three-way connector $T_{1-1}$ and flows upon separation so as to be introduced in the three-way connector $T_{1-2}$ and GC second dimensional column 56. As a result, the sample flowing out from the GC first dimensional column 55 is introduced in the three-way connector $T_{2-1}$, without being introduced in the GC second dimensional column 56. The sample separated in the GC first dimensional column 55 is separated and introduced via the three-way connectors $T_{2-3}$, $T_{2-2}$, $T_{2-3}$ in the mass analyzer 43 and olfactory device 44. Mass analysis is carried out in the mass analyzer 43 and at the same time, the detection of odorous substance is carried out with the olfactory device 44. In the three-way connector $T_{2-2}$, the moving phase gas that has passed through the GC second dimensional column 56 is mixed, but sample components are not admixed to the moving phase gas and produce no adverse effect on the detection in the mass analyzer 43 and olfactory device 44. The analysis using only the GC first dimensional column is thus carried out in the present device.

Figure 1:
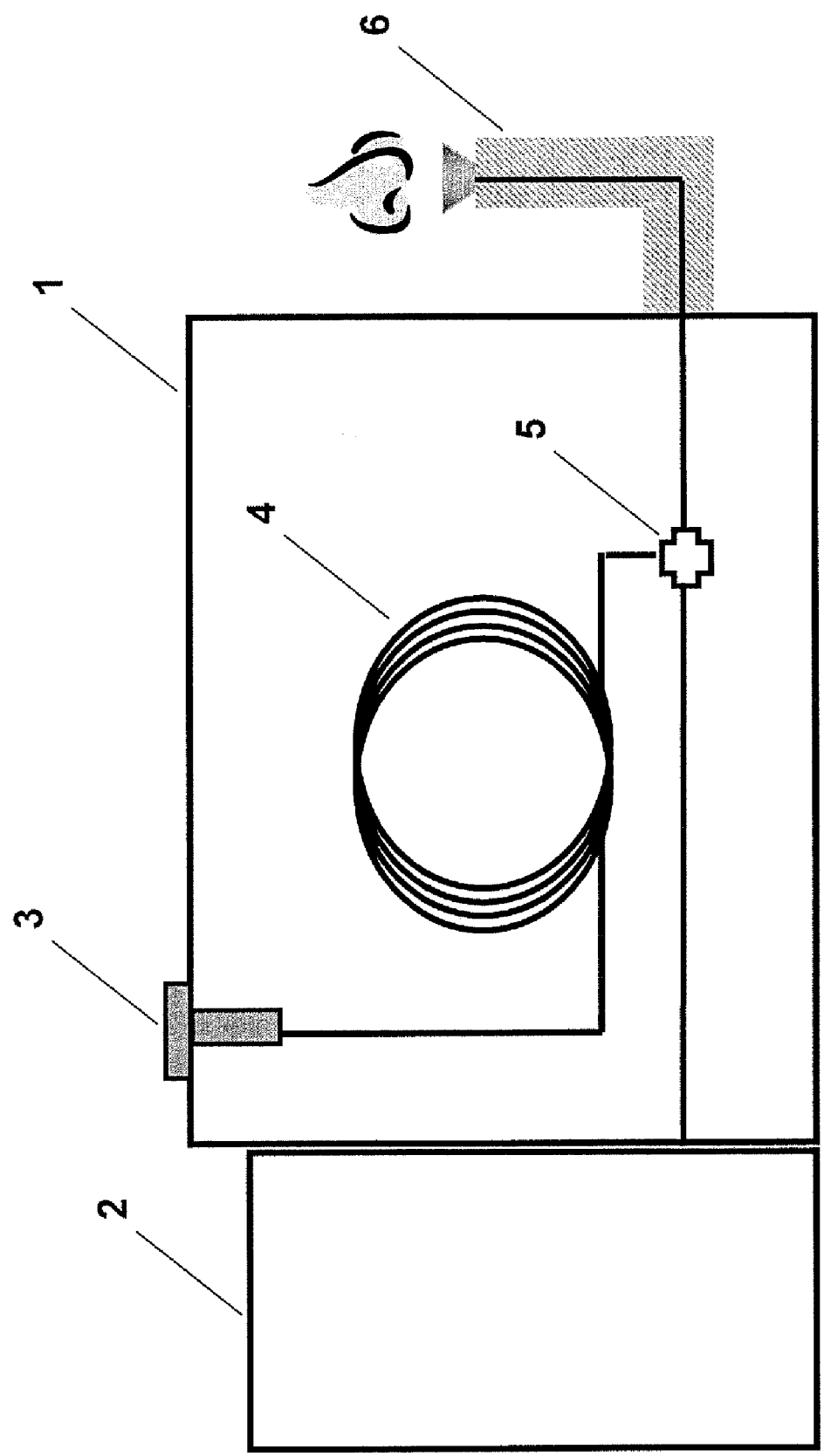
FIG. 1 illustrates an olfactory device using one-dimensional gas chromatograph-mass spectrometer analyzer; 1 refer to gas chromatography, 2 refer to mass analyzer, 3 refer to sample injection port, 4 refer to column, 5 refer to splitter, 6 refer to olfactory device.
Figure 2:
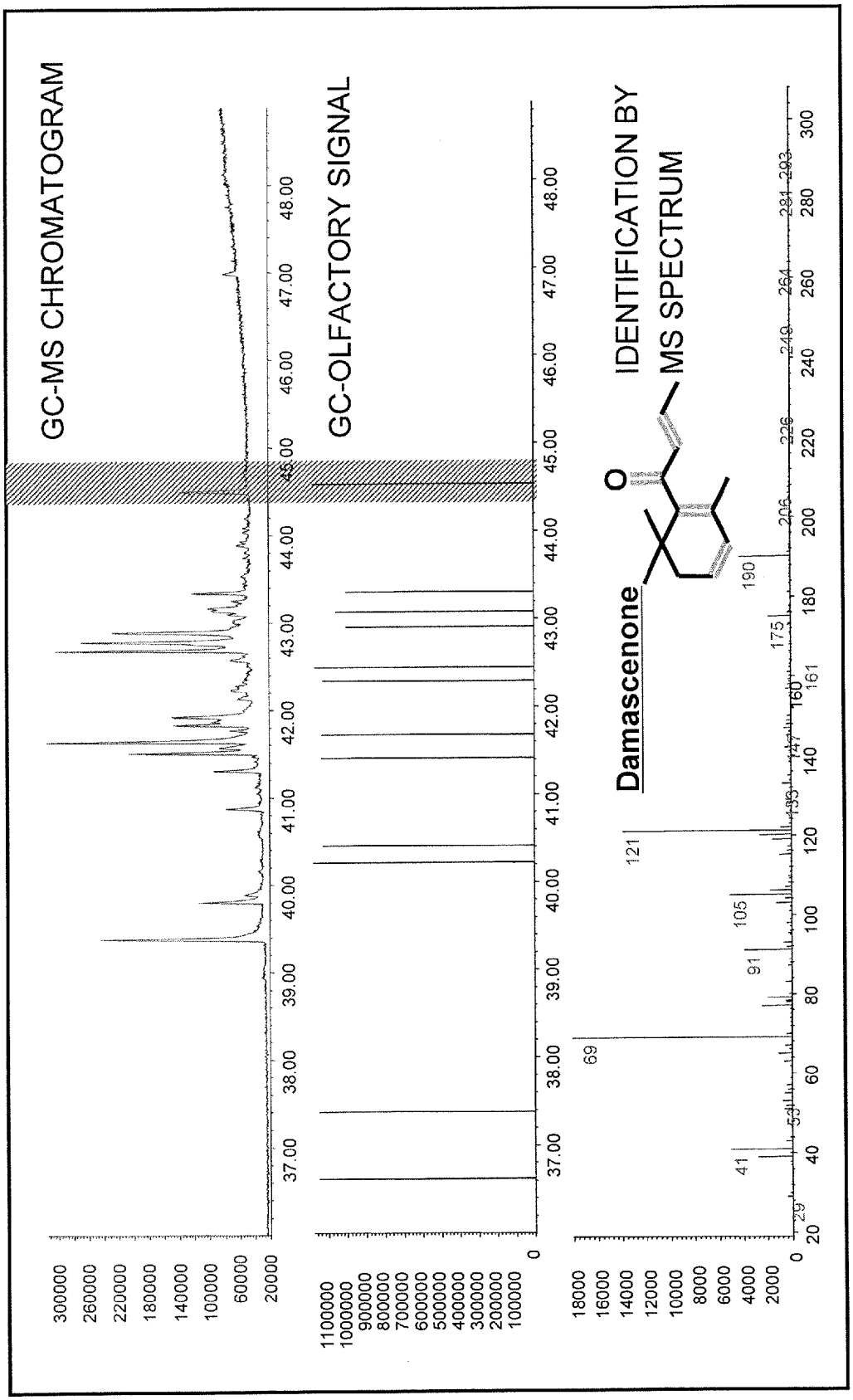
FIG. 2 shows an analysis example obtained employing an olfactory device using one-dimensional gas chromatograph-mass spectrometer analyzer.
Figure 3:
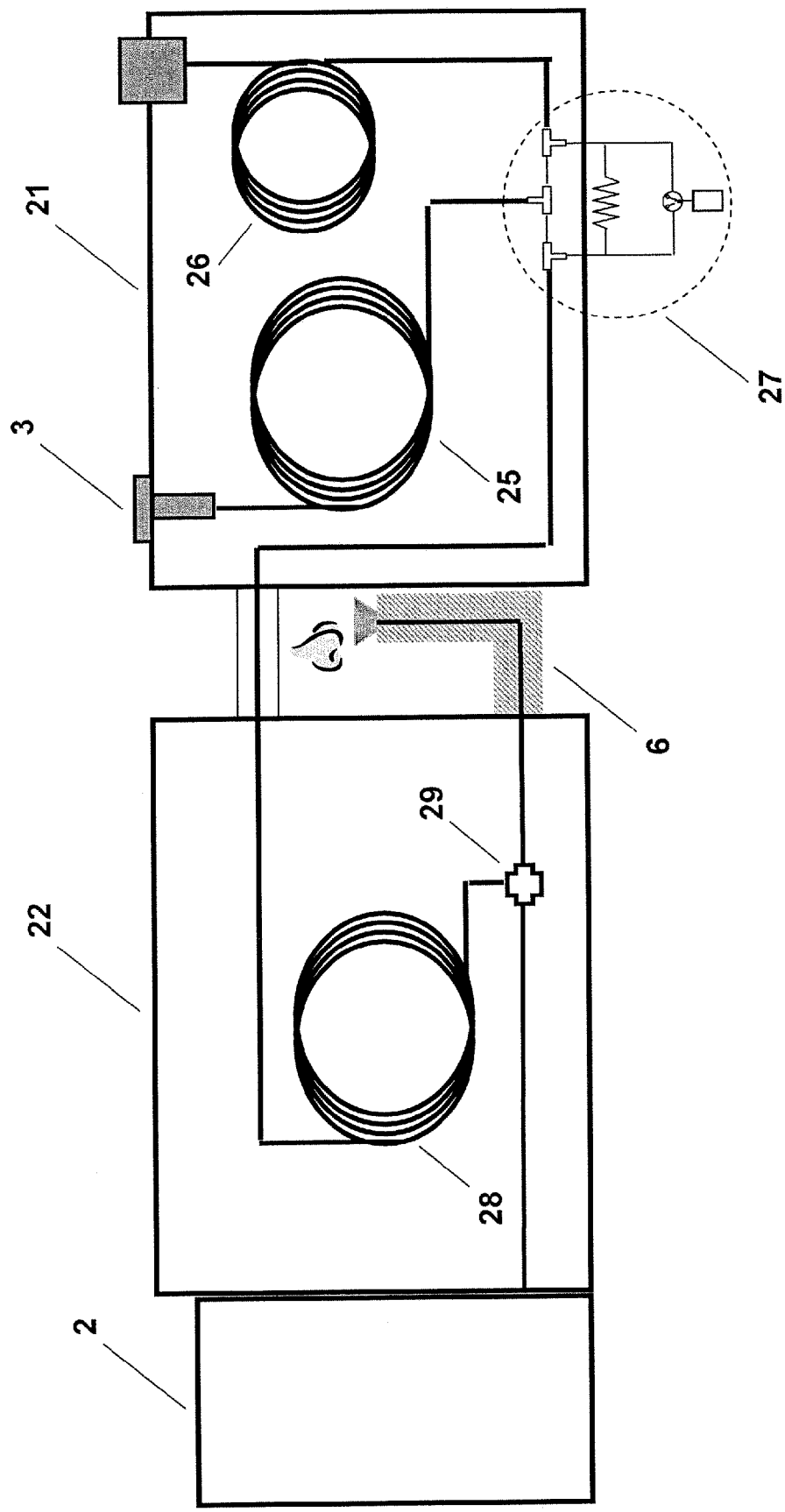
FIG. 3 illustrates an olfactory device using two-dimensional gas chromatograph-mass spectrometer analyzer; 21 refer to first dimensional gas chromatography, 22 refer to second dimensional gas chromatography, 25 refer to GC first dimensional column, 26 refer to resistant tube, 27 refer to switching device of flow by means of DEANS, 28 refer to GC second dimensional column.
Figure 4:
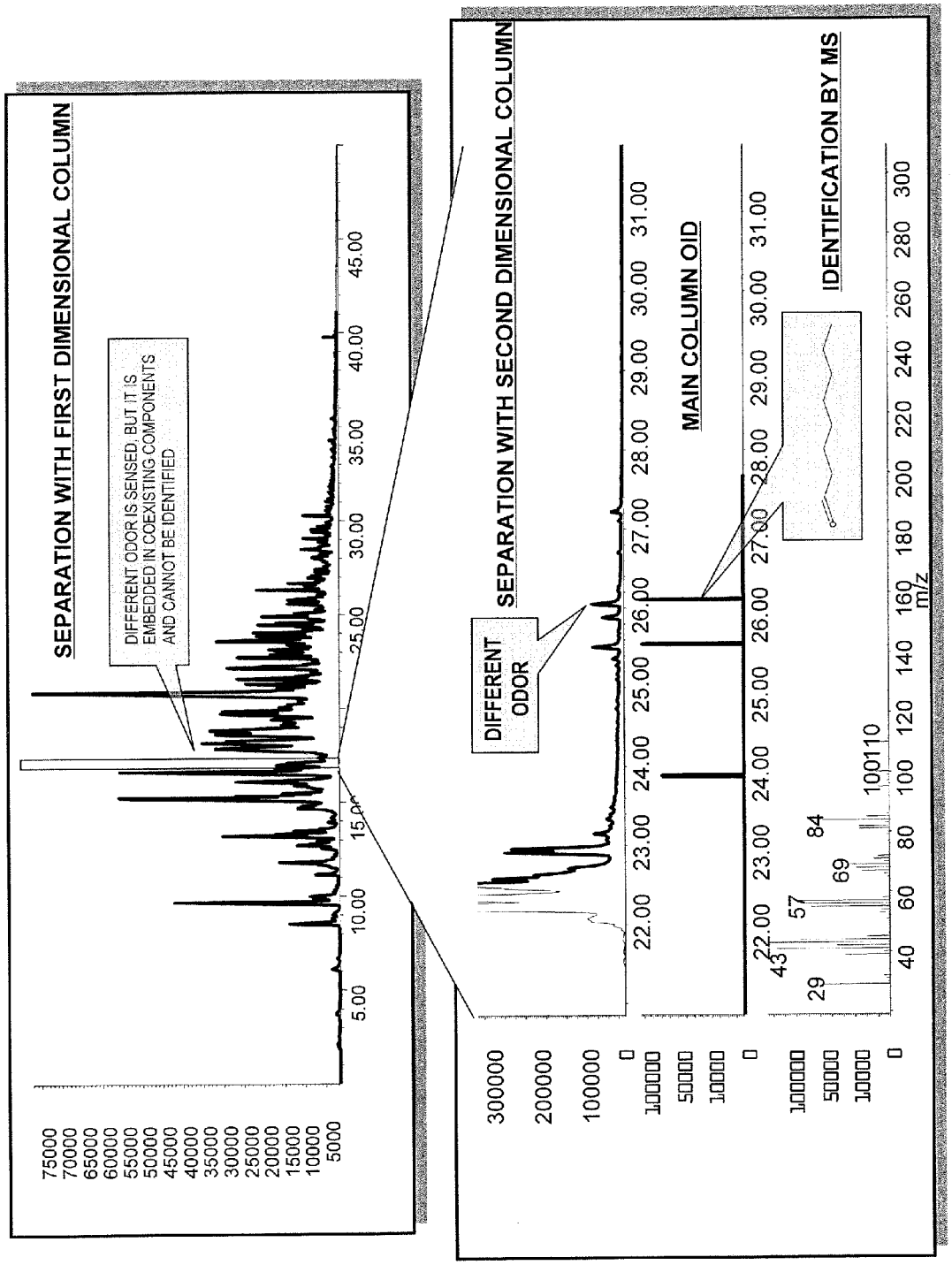
FIG. 4 shows an analysis example relating to the case in which two-dimensional chromatograph is used.
Figure 7:
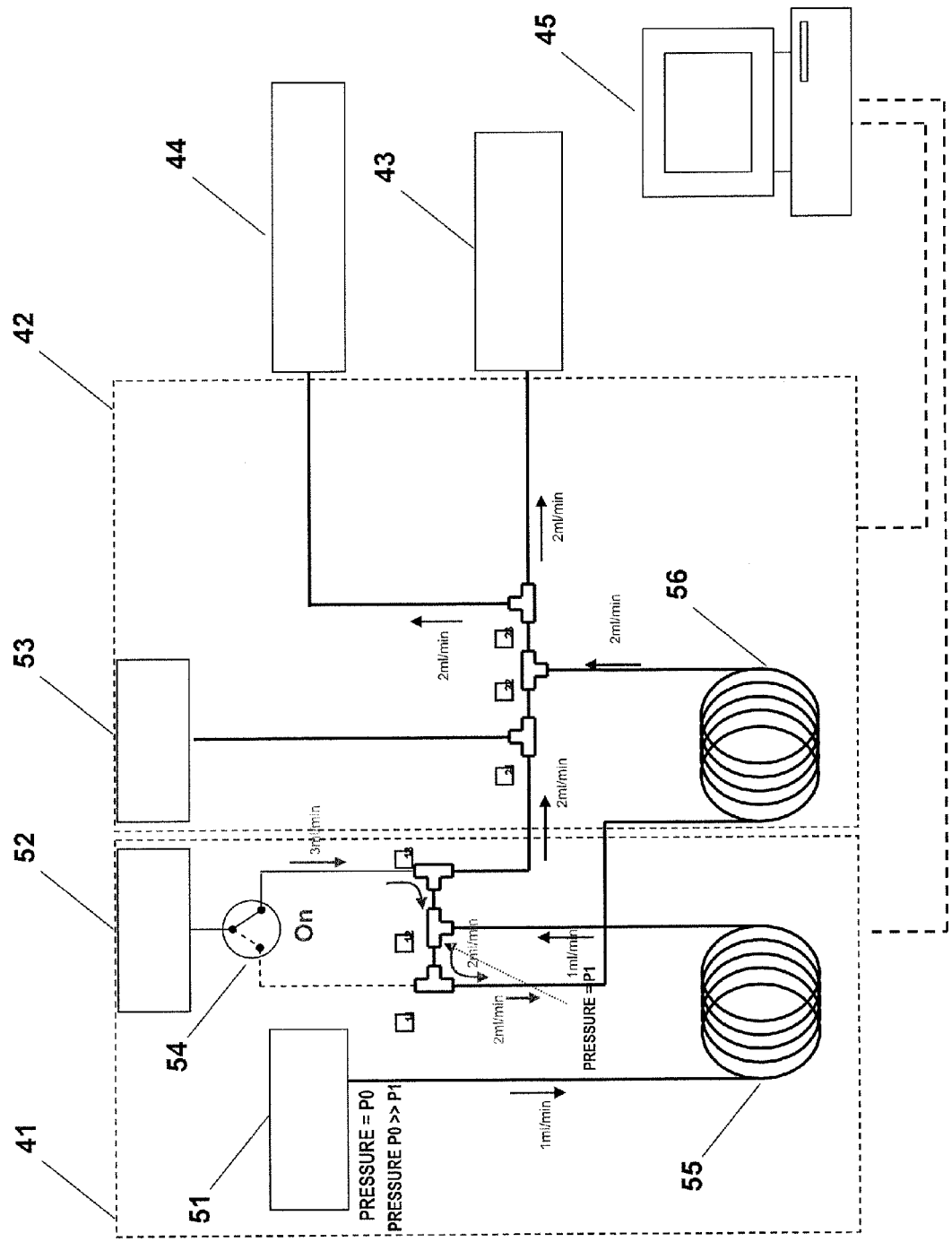
FIG. 7 illustrates the operation in accordance with the present invention.
Figure 8:
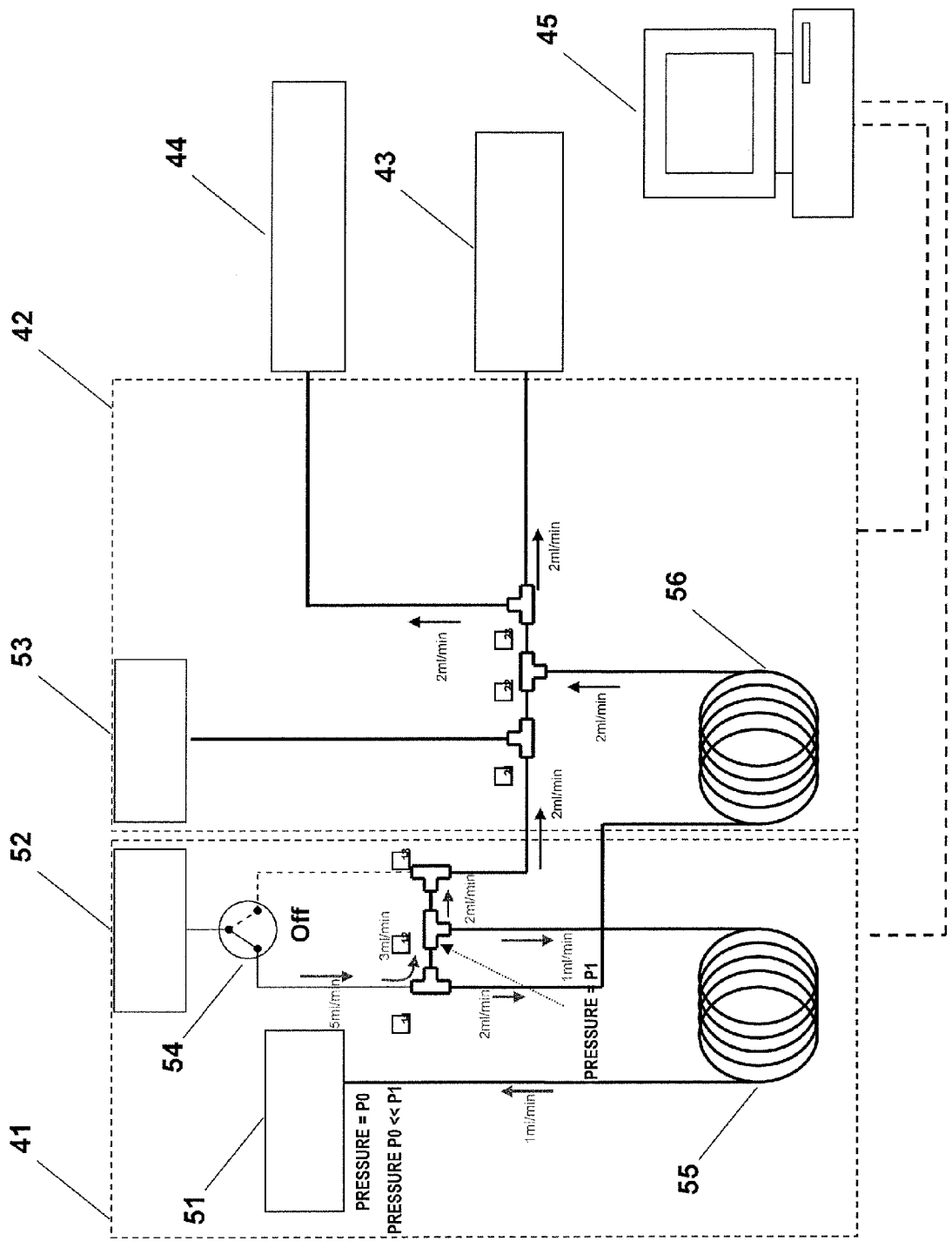
FIG. 8 illustrates the operation in accordance with the present invention.

The analysis method that uses the GC second dimensional column in addition to the GC first dimensional column will be described below. When different odors are sensed, but they are embedded in a common component and cannot be identified in the separation by the GC first dimensional column, as shown in FIG. 4, for example, the target sample is separated using the GC first dimensional column, and the separated sample portion is then introduced in the GC second dimensional column. Thus, as shown in FIG. 6, first, the sample is separated with the GC first dimensional column 55. Then, when the retention time of a portion for which a different odor has been sensed in the earlier analysis is reached, the solenoid valve 54 is switched to ON, as shown in FIG. 7. As a result, the moving phase gas supplied from the pressure control device 52 is introduced in the three-way connector $T_{1-3}$, and the moving phase gas containing the target sample component and supplied from the GC first dimensional column 55 is introduced in the three-way connector $T_{1-2}$, mixed with the moving phase gas introduced from the three-way connector $T_{1-3}$, and supplied to the three-way connector $T_{1-1}$. In this case, part of the moving phase gas supplied from the pressure control device 52 to the three-way connector $T_{1-3}$ is introduced in the three-way connector $T_{1-2}$, and the remaining moving phase gas is introduced in the three-way connector $T_{2-1}$. The sample gas exiting from the three-way connector $T_{1-1}$ is introduced in the GC second dimensional column 56, separated into components, and introduced in the three-way connector $T_{2-2}$. In the three-way connector $T_{2-2}$, the moving phase gas supplied from the three-way connector $T_{1-3}$ and the sample gas are mixed, and the mixture is supplied via the three-way connector $T_{2-3}$ in the mass analyzer 43 and olfactory device 44. As a result, as shown in FIG. 4, the odor components can be identified using the second dimensional column. Once the introduction of the sample component in the GC second dimensional column 56 has been completed, the solenoid valve 54 is again switched OFF and, at the same time, the pressure P0 of the sample injection port 51 equipped with a pressure control device is made lower than the pressure P1 of the three-way connector $T_{1-2}$. As a result, other sample components remaining in the GC first dimensional column 55 are returned to the sample injection port 51 equipped with a pressure control device and discharged. As a result, the other components, which are not the target component, can be prevented from being introduced in the mass analyzer 43 and olfactory device 44. These operations of the valve and pressure control device may be controlled with a control computer 45.

Thus, by using one device it is possible to perform GC one-dimensional odor analysis and GC two-dimensional odor analysis by a simple switching operation, without changing the device configuration.

Figure 9:
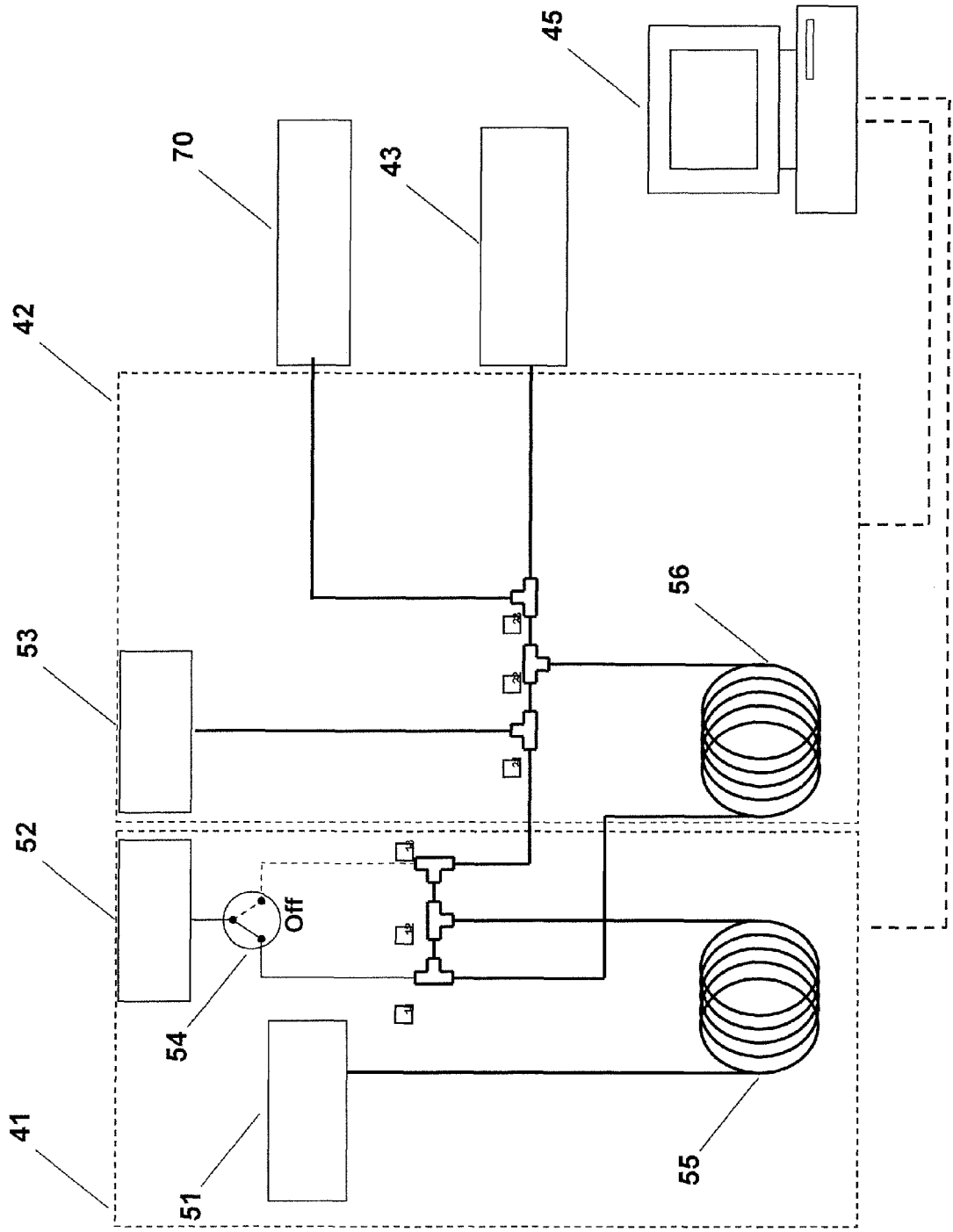
FIG. 9 illustrates another embodiment of the present invention.

Another embodiment of the present invention will be described below. In this embodiment of the present invention, a GC detector 70 is connected instead of the olfactory device 44 shown in FIG. 6 (see FIG. 9). The operation of devices shown in FIG. 9, other than the GC detector 70, is identical to that of the devices shown in FIG. 6, and the explanation thereof will be omitted. In the present device, the GC detector 70 can perform GC detection together with the mass analyzer 43 with respect to the sample separated using only the GC first dimensional column 55. Further, once the solenoid valve 54 is switched, the detector can also perform GC detection together with the mass analyzer 43 with respect to the sample subjected to additional separation with respect to a sample with specific components by the GC second dimensional column 56.

The detection unit in the GC detector 70 is not particularly limited, and examples of suitable detectors include an FID (hydrogen flame ionization detector), an NPD (nitrogen phosphorus detector), an ECD (electron capture detector), an SCD (sulfur flame chemoluminescence detector), an NCD (nitrogen flame chemoluminescence detector), an AED (atomic emission detector), an FPD (flame photometric detector), and a PFPD (pulsed flame photometric detector).

Figure 10:
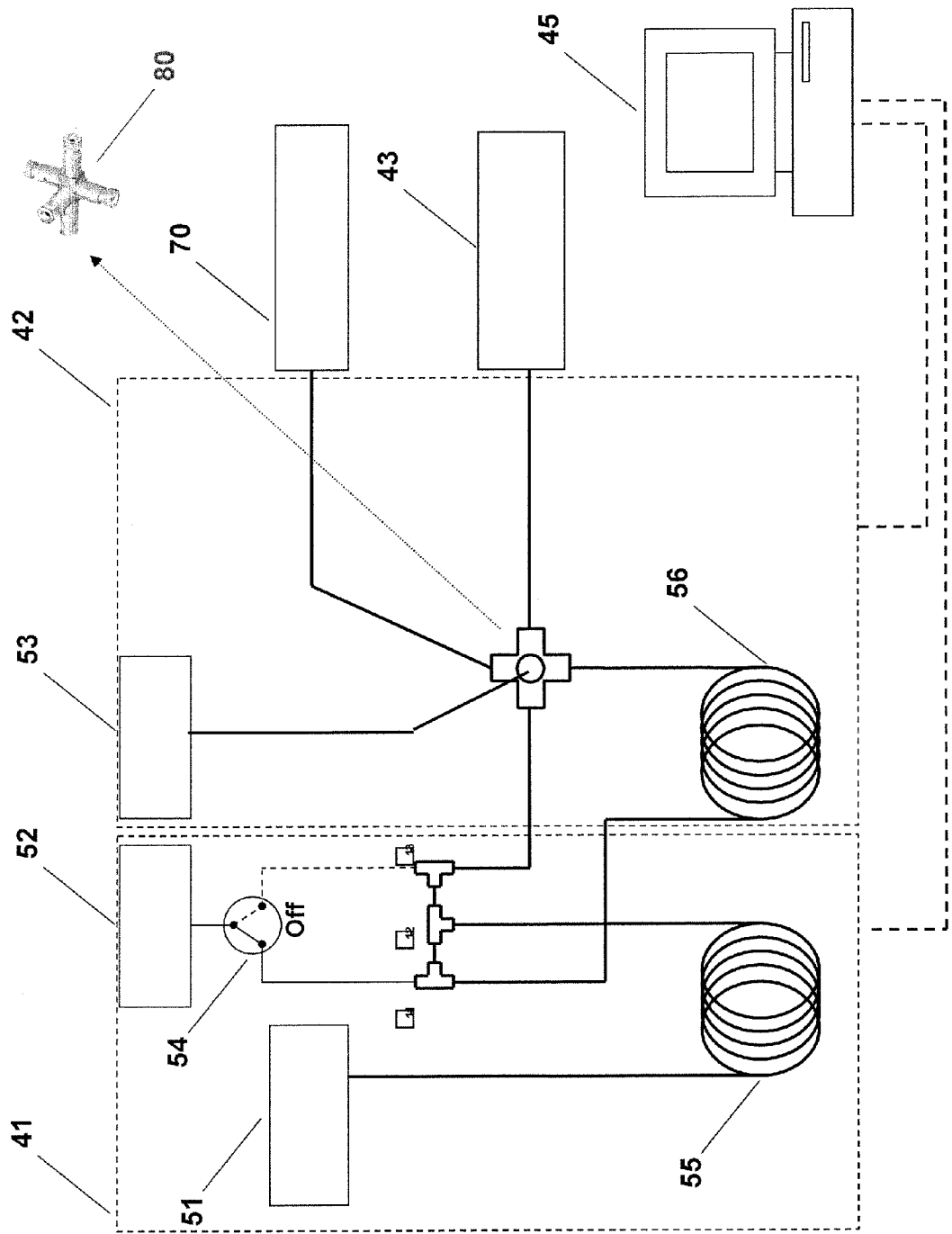
FIG. 10 illustrates another embodiment of the present invention.

Yet another embodiment of the device in accordance with the present invention will be described below. FIG. 10 shows an example of the analyzer in accordance with the present invention in which a five-way connector 80 is used instead of the three-way connectors $T_{2-1}$, $T_{2-2}$, $T_{2-3}$ shown in FIG. 9. Replacing three connectors with the five-way connector 80 makes it possible to simplify the device. An odor analyzer can be obtained by using the olfactory device 44 shown in FIG. 6 instead of the GC detector 70 shown in FIG. 10.

Figure 11:
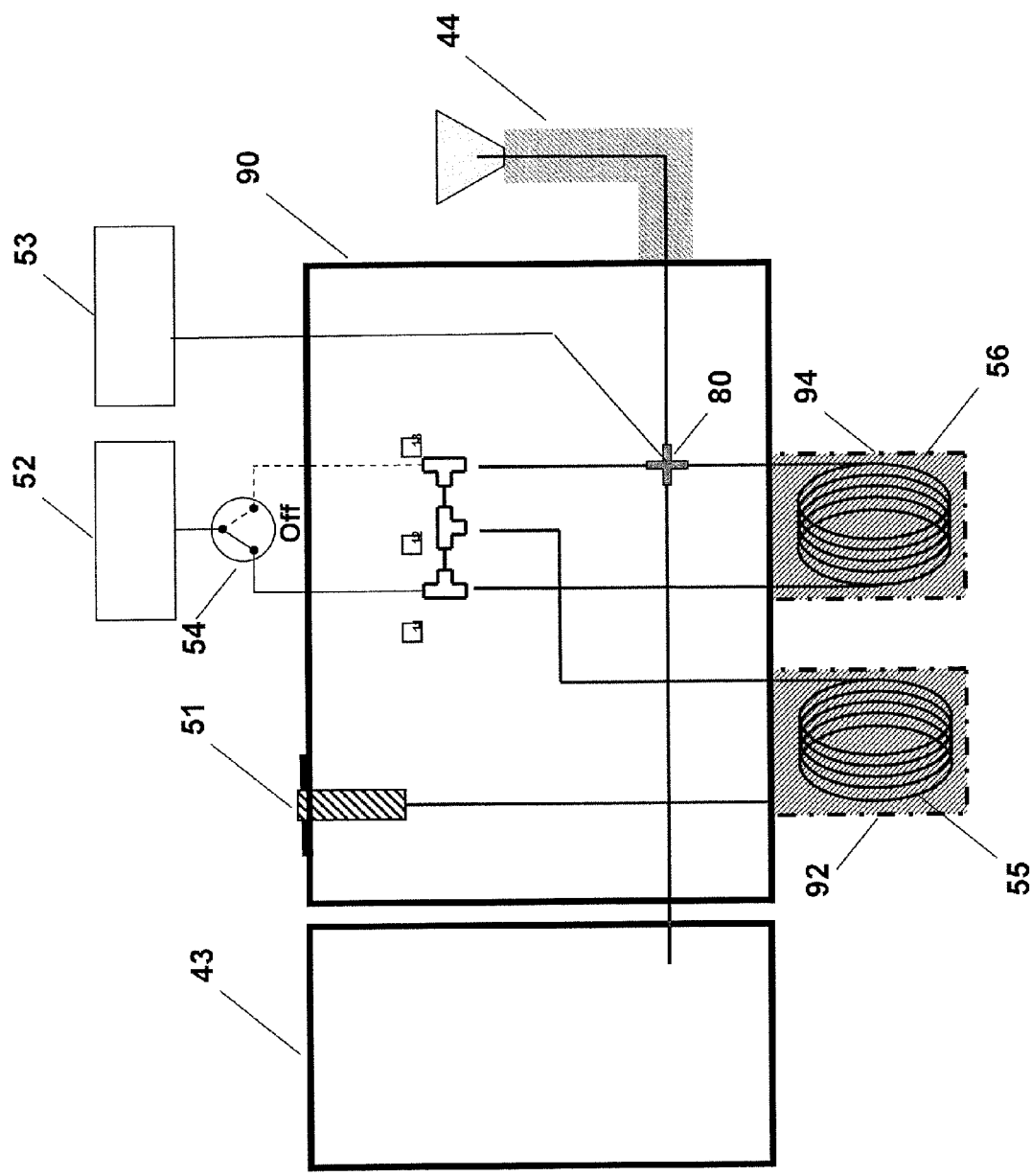
FIG. 11 illustrates another embodiment of the present invention.

Yet another embodiment of the present invention will be described below with reference to FIG. 11. By contrast with the configuration shown in FIG. 6, the GC first dimensional column 55 and GC second dimensional column 56 protrude from a flow channel control unit 90 and temperature regulated with column heaters 92 and 94, respectively. Further, by contrast with the configuration shown in FIG. 6, a five-way connector 80 is used instead of the three-way connectors $T_{2-1}$, $T_{2-2}$, $T_{2-3}$. With such a configuration a simple device can be obtained.

Figure 12:
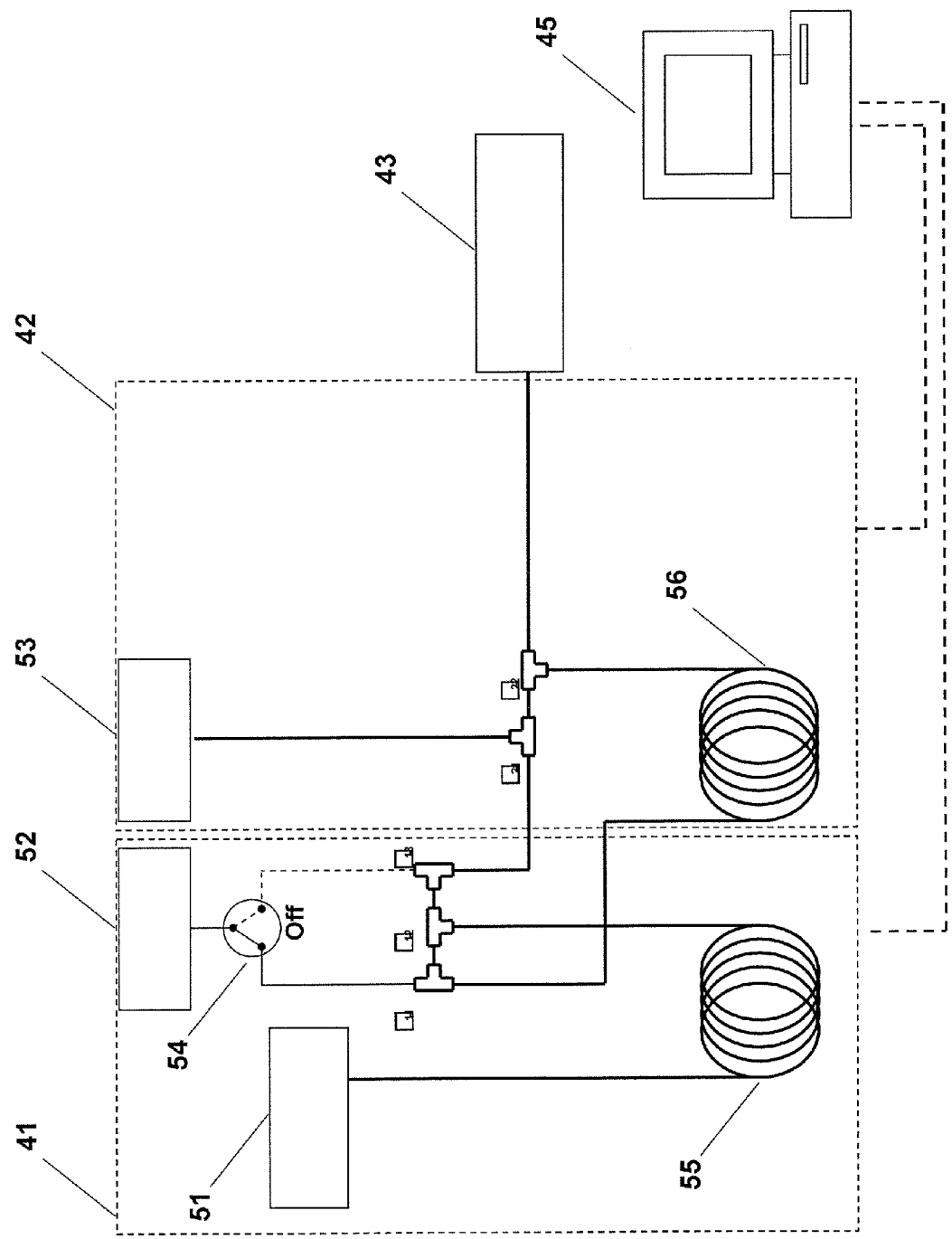
FIG. 12 illustrates another embodiment of the present invention.

Still another embodiment of the device in accordance with the present invention will be described below. FIG. 12 shows schematically the analyzer in accordance with the present invention. Referring to FIG. 12, the analyzer in accordance with the present invention includes: (a) a sample injection port 51 equipped with a pressure control device; (b) a GC first dimensional column 55 connected to the sample injection port 51 equipped with a pressure control device; (c) a three-way connector $T_{1-2}$ connected to the GC first dimensional column 55; (d) three-way connectors $T_{1-1}$, $T_{1-3}$, each connected to the three-way connector $T_{1-2}$; (e) a solenoid valve 54 connected to the three-way connectors $T_{1-1}$, $T_{1-3}$; (f) a pressure control device 52 connected to the solenoid valve 54; (g) a three-way connector $T_{2-1}$ connected to the three-way connector $T_{1-3}$; (h) a pressure control device 53 connected to the three-way connector $T_{2-1}$; (i) a three-way connector $T_{2-2}$ connected to the three-way connector $T_{2-1}$; (j) a mass analyzer 43 connected to the three-way connector $T_{2-2}$; and (k) a GC second dimensional column 56 connected to the three-way connector $T_{1-1}$ and the three-way connector $T_{2-2}$. The sample injection port 51, pressure control device 52, solenoid valve 54, three-way connectors $T_{1-1}$, $T_{1-2}$, $T_{1-3}$, and CG first dimensional column 55 constitute a first dimensional gas chromatograph 41. The pressure control device 53, three-way connectors $T_{2-1}$, $T_{2-2}$, and GC second dimensional column 56 constitute a second dimensional gas chromatograph 42. The odor component analyzer in accordance with the present invention is configured by a control computer 45 connected to the gas chromatographs 41 and 42.

The operation of the analyzer in accordance with the present invention will be described below. First, an analysis method based only on a GC first dimensional column will be described. Referring to FIG. 12, a sample that is the analysis object is injected from a sample injection port 51 equipped with a pressure control device. A pressure P0 in the sample injection port in this case is set higher than a pressure P1 in the three-way connector $T_{1-2}$. The sample injected from the sample injection port equipped with a pressure control device is introduced in the GC first dimensional column, separated correspondingly to the retention time, passes through the three-way connector $T_{1-2}$ and is introduced in the second dimensional gas chromatograph 42 via the three-way connector $T_{1-3}$. The switch of the solenoid valve 54 is in the OFF state, a moving phase gas flowing in from the pressure control device 52 passes through the three-way connector $T_{1-1}$ and flows upon separation so as to be introduced in the three-way connector $T_{1-2}$ and GC second dimensional column 56. As a result, the sample flowing out from the GC first dimensional column 55 is introduced in the three-way connector $T_{2-1}$, without being introduced in the GC second dimensional column 56. The sample separated in the GC first dimensional column 55 is separated and introduced via the three-way connectors $T_{2-1}$, $T_{2-2}$ in the mass analyzer 43. Mass analysis is carried out in the mass analyzer 43. In the three-way connector $T_{2-2}$, the moving phase gas that has passed through the GC second dimensional column 56 is mixed, but sample components are not admixed to the moving phase gas and produce no adverse effect on the detection in the mass analyzer 43. The analysis using only the GC first dimensional column is thus carried out in the present device.

The analysis method that uses the GC second dimensional column in addition to the GC first dimensional column will be described below. When the number of coexisting components is large and they cannot be identified by the separation with the GC first dimensional column, the target sample is separated using the GC first dimensional column, and the separated sample portion is then introduced in the GC second dimensional column. Thus, as shown in FIG. 12, first, the sample is separated with the GC first dimensional column 55. Then, when the retention time of a coexisting portion of the earlier analysis is reached, the solenoid valve 54 is switched to ON. As a result, the moving phase gas supplied from the pressure control device 52 is introduced in the three-way connector $T_{1-3}$, and the moving phase gas containing the target sample component and supplied from the GC first dimensional column 55 is introduced in the three-way connector $T_{1-2}$, mixed with the moving phase gas introduced from the three-way connector $T_{1-3}$, and supplied to the three-way connector $T_{1-1}$. In this case, part of the moving phase gas supplied from the pressure control device 52 to the three-way connector $T_{1-3}$ is introduced in the three-way connector $T_{1-2}$, and the remaining moving phase gas is introduced in the three-way connector $T_{2-1}$. The sample gas exiting from the three-way connector $T_{1-1}$ is introduced in the GC second dimensional column 56, separated into components, and introduced in the three-way connector $T_{2-2}$. In the three-way connector $T_{2-2}$, the moving phase gas supplied from the three-way connector $T_{1-3}$ and the sample gas are mixed, and the mixture is supplied in the mass analyzer 43. As a result, the target component can be identified using the second dimensional column. Once the introduction of the sample component in the GC second dimensional column 56 has been completed, the solenoid valve 54 is again switched OFF and, at the same time, the pressure P0 of the sample injection port 51 equipped with a pressure control device is made lower than the pressure P1 of the three-way connector $T_{1-2}$. As a result, other sample components remaining in the GC first dimensional column 55 are returned to the sample injection port 51 equipped with a pressure control device and discharged. As a result, the other components, which are not the target component, can be prevented from flowing into the mass analyzer 43. These operations of the valve and pressure control device may be controlled with a control computer 45.

Thus, by using one device it is possible to perform GC one-dimensional analysis and GC two-dimensional analysis by a simple switching operation, without changing the device configuration.

In accordance with the present invention, one-dimensional GC-MS/olfactory analysis and two-dimensional GC-MS/olfactory analysis are freely performed in a two-dimensional GC-MS/olfactory device by a simple switching operation, without changing the device configuration. Furthermore, in accordance with the present invention, the one-dimensional GC analysis and two-dimensional GC analysis can be performed by switching in applications other than odor analysis.

What is claimed is:
1. An odor component analyzer, comprising:
(a) a sample injection port equipped with a pressure control device;
(b) a GC first dimensional column connected to the sample injection port;
(c) a three-way connector $T_{1-2}$ connected to the GC first dimensional column;
(d) three-way connectors $T_{1-1}$, $T_{1-3}$, each connected to the three-way connector $T_{1-2}$;
(e) a solenoid valve connected to the three-way connectors $T_{1-1}$, $T_{1-3}$ and serving to adjust flow channels of the three-way connectors $T_{1-1}$, $T_{1-3}$;
(f) a first pressure control device connected to the solenoid valve;
(g) a three-way connector $T_{2-1}$ connected to the three-way connector $T_{1-3}$;
(h) a second pressure control device connected to the three-way connector $T_{2-1}$;
(i) a three-way connector $T_{2-2}$ connected to the three-way connector $T_{2-1}$;
(j) a three-way connector $T_{2-3}$ connected to the three-way connector $T_{2-2}$;
(k) a mass analyzer and an olfactory device, each connected to the three-way connector $T_{2-3}$; and
(l) a GC second dimensional column connected to the three-way connector $T_{1-1}$ and the three-way connector $T_{2-2}$.

2. The odor component analyzer according to claim 1, further comprising a device for adjusting a temperature of only a first dimensional column section and/or only a second dimensional column section.

3. An analyzer, comprising:
   (a) a sample injection port equipped with a pressure control device;
   (b) a GC first dimensional column connected to the sample injection port;
   (c) a three-way connector $T_{1-2}$ connected to the GC first dimensional column;
   (d) three-way connectors $T_{1-1}$, $T_{1-3}$, each connected to the three-way connector $T_{1-2}$;
   (e) a solenoid valve connected to the three-way connectors $T_{1-1}$, $T_{1-3}$ and serving to adjust flow channels of the three-way connectors $T_{1-1}$, $T_{1-3}$;
   (f) a first pressure control device connected to the solenoid valve;
   (g) a three-way connector $T_{2-1}$ connected to the three-way connector $T_{1-3}$;
   (h) a second pressure control device connected to the three-way connector $T_{2-1}$;
   (i) a three-way connector $T_{2-2}$ connected to the three-way connector $T_{2-1}$;
   (j) a three-way connector $T_{2-3}$ connected to the three-way connector $T_{2-2}$;
   (k) a mass analyzer and a GC detector, each connected to the three-way connector $T_{2-3}$; and
   (l) a GC second dimensional column connected to the three-way connector $T_{1-1}$ and the three-way connector $T_{2-2}$.

4. The analyzer according to claim 3, further comprising a device for adjusting a temperature of only a first dimensional column section and/or only a second dimensional column section.

5. The analyzer according to claim 3, wherein the GC detector is selected from a group consisting of an FID, an NPD, an ECD, an SCD, an NCD, an AED, an FPD, and a PFPD.

6. An analyzer, comprising:
   (a) a sample injection port equipped with a pressure control device;
   (b) a GC first dimensional column connected to the sample injection port;
   (c) a three-way connector $T_{1-2}$ connected to the GC first dimensional column;
   (d) three-way connectors $T_{1-1}$, $T_{1-3}$, each connected to the three-way connector $T_{1-2}$;
   (e) a solenoid valve connected to the three-way connectors $T_{1-1}$, $T_{1-3}$ and serving to adjust flow channels of the three-way connectors $T_{1-1}$, $T_{1-3}$;
   (f) a first pressure control device connected to the solenoid valve;
   (g) a three-way connector $T_{2-1}$ connected to the three-way connector $T_{1-3}$;
   (h) a second pressure control device connected to the three-way connector $T_{2-1}$;
   (i) a three-way connector $T_{2-2}$ connected to the three-way connector $T_{2-1}$;
   (j) a mass analyzer connected to the three-way connector $T_{2-2}$; and
   (k) a GC second dimensional column connected to the three-way connector $T_{1-1}$ and the three-way connector $T_{2-2}$.

7. The analyzer according to claim 6, further comprising a device for adjusting a temperature of only a first dimensional column section and/or only a second dimensional column section.

\* \* \* \* \*